(12) United States Patent
Iriyama et al.

(10) Patent No.: US 8,609,075 B2
(45) Date of Patent: Dec. 17, 2013

(54) HEPARANASE ACTIVITY INHIBITOR

(75) Inventors: Shunsuke Iriyama, Yokohama (JP);
Hirotada Fukunishi, Yokohama (JP);
Masaru Suetsugu, Yokohama (JP);
Satoshi Amano, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/261,244

(22) PCT Filed: Sep. 29, 2010

(86) PCT No.: PCT/JP2010/066998
§ 371 (c)(1),
(2), (4) Date: Mar. 29, 2012

(87) PCT Pub. No.: WO2011/040496
PCT Pub. Date: Apr. 7, 2011

(65) Prior Publication Data
US 2012/0183481 A1    Jul. 19, 2012

(30) Foreign Application Priority Data
Sep. 30, 2009    (JP) .................................. 2009-228406

(51) Int. Cl.
*A61K 8/49*        (2006.01)
*A61K 31/4166*     (2006.01)
*A61K 31/4015*     (2006.01)
*A61Q 19/02*       (2006.01)
*A61P 17/00*       (2006.01)

(52) U.S. Cl.
USPC ............................ 424/62; 514/392; 514/424

(58) Field of Classification Search
None
See application file for complete search history.

(56) References Cited

U.S. PATENT DOCUMENTS

| | | | |
|---|---|---|---|
| 4,049,650 A | 9/1977 | White, Jr. | |
| 4,731,453 A | 3/1988 | Nagata et al. | |
| 5,011,621 A | 4/1991 | Sullivan | |
| 5,594,149 A | 1/1997 | Naruse et al. | |
| 7,238,260 B2 | 7/2007 | Kahn et al. | |
| 2005/0287089 A1* | 12/2005 | Mahalingam et al. | 424/62 |
| 2009/0136595 A1* | 5/2009 | Shah et al. | 424/649 |
| 2009/0285868 A1 | 11/2009 | Richard et al. | |

FOREIGN PATENT DOCUMENTS

| | | |
|---|---|---|
| DE | 2746550 A1 | 4/1978 |
| EP | 2 119 429 A1 | 11/2009 |
| JP | 2901297 B2 | 3/1999 |
| JP | 11-335235 A | 12/1999 |
| JP | 2000-503660 A | 3/2000 |
| JP | 2001-163794 A | 6/2001 |
| JP | 2004-526758 A | 9/2004 |
| JP | 2007-277149 A | 10/2007 |
| JP | 2008-303185 A | 12/2008 |
| JP | 2008-303186 A | 12/2008 |
| JP | 2008-303187 A | 12/2008 |
| WO | WO 90/00407 A1 | 1/1990 |
| WO | WO 97/25969 A1 | 7/1997 |
| WO | WO 02/083088 A1 | 10/2002 |
| WO | WO 03/084302 A2 | 10/2003 |
| WO | WO 2009/122540 A1 | 10/2009 |
| WO | WO 2009/123215 A1 | 10/2009 |

OTHER PUBLICATIONS

Kajiya et al., "Vascular Endothelial Growth Factor-A Mediates Ultraviolet B-Induced Impairment of Lymphatic Vessel Function," The America Journal of Pathology, Oct. 2006, 169(4):1496-1503.
Vlodavsky et al., "Mammalian heparanase: involvement in cancer metastasis, angiogenesis and normal development," Cancer Biology, 2002, 12:121-129.

* cited by examiner

*Primary Examiner* — Frederick Krass
*Assistant Examiner* — Celeste A Roney
(74) *Attorney, Agent, or Firm* — Foley & Lardner LLP

(57) ABSTRACT

A heparanase activity inhibitor comprising, as an active ingredient, a cyclic carboxamide derivative represented by formula (I):

$$\underset{(CH_2)_n}{\underset{|}{X}}\!\!\diagdown\!\!\underset{N-R^1}{\overset{O}{\|}}\!\!\diagup \quad (I)$$

wherein n is an integer of 1 to 3, $R^1$ is hydrogen or a C1-6 hydrocarbon group optionally substituted with hydroxyl, X is —$CH_2$— or a group represented by —$N(R^2)$—, and $R^2$ is hydrogen or a C1-6 hydrocarbon group optionally substituted with hydroxyl,
or a salt thereof.

1 Claim, 13 Drawing Sheets

FIG.3
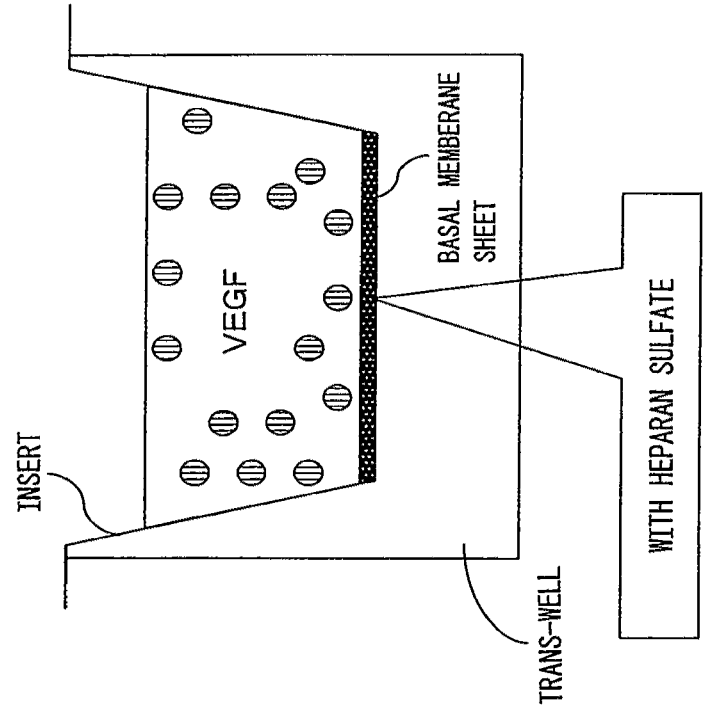
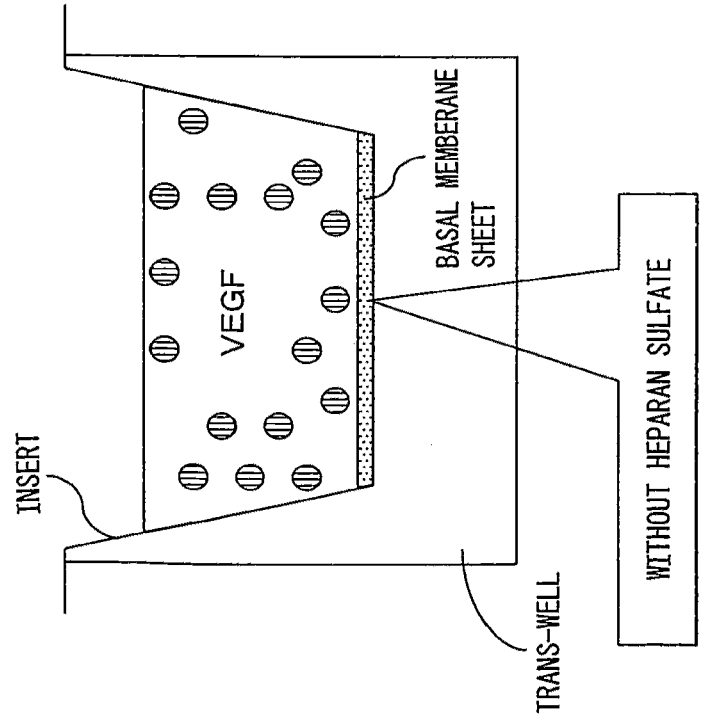

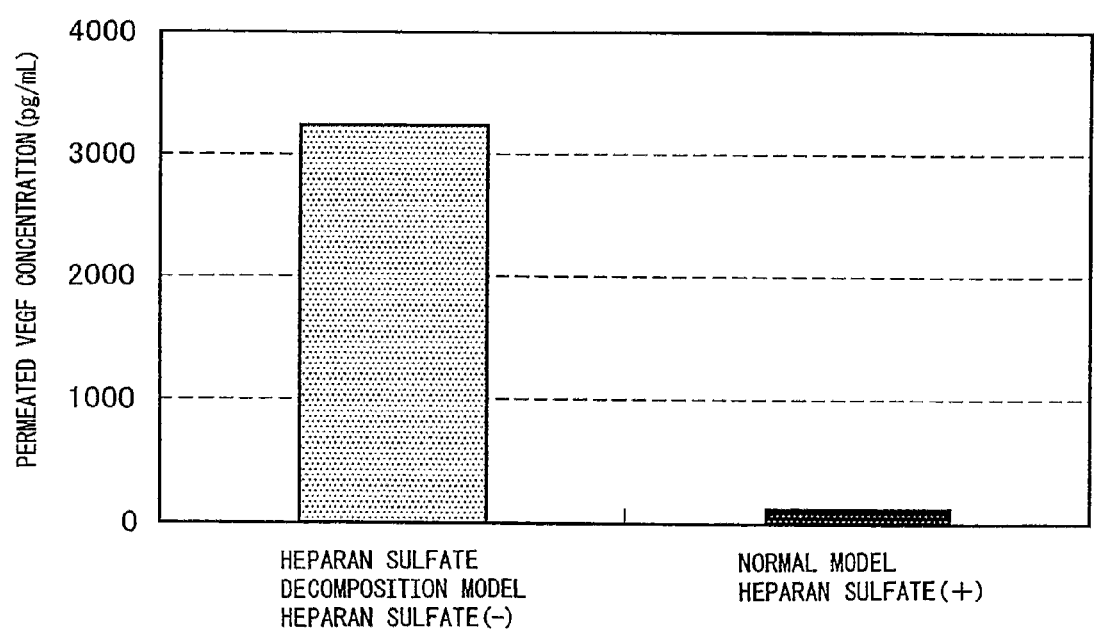
F I G.4

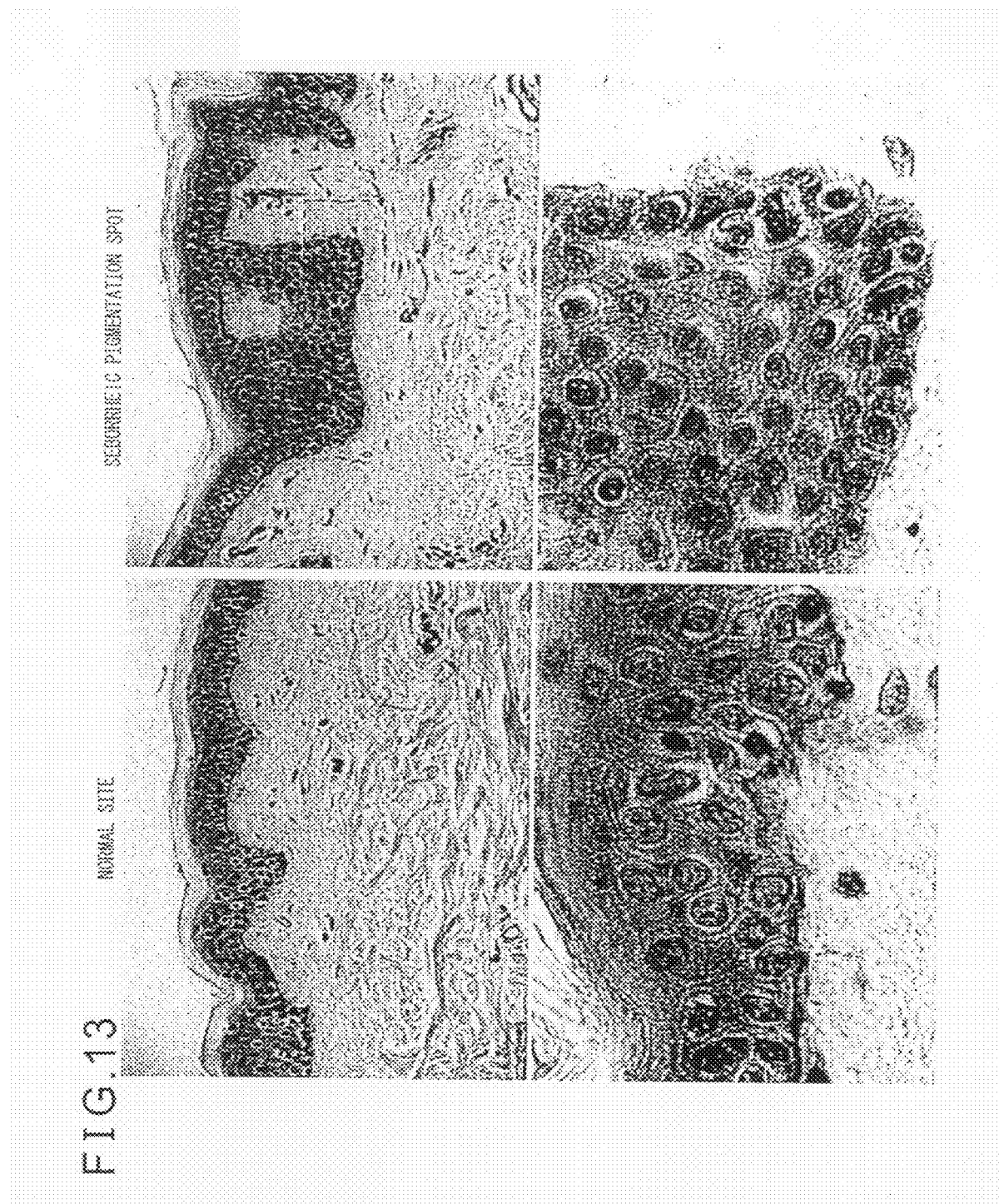

HEPARANASE ACTIVITY INHIBITOR

CROSS-REFERENCE TO RELATED APPLICATIONS

This application is a National Stage application of PCT/JP2010/066998, filed Sep. 29, 2010, which claims priority from Japanese application JP 2009-228406, filed Sep. 30, 2009.

TECHNICAL FIELD

The present invention relates to an external preparation for skin containing a cyclic carboxamide derivative of formula (I) as an active ingredient, and particularly to a heparanase inhibitor that, when used as a cosmetic, inhibits activation of heparanase in the skin, inhibits skin alteration occurring with failure of control of growth factors, by supporting heparan sulfate, and allows the condition of youthful skin to be maintained, while also exhibiting a whitening effect.

BACKGROUND ART

Anti-aging research has continued to advance in recent years. Somatic aging is a major cause of skin aging from a macroscopic viewpoint, but other causes such as oxidation, dryness and sunlight (ultraviolet rays) are also direct factors related to skin aging. The specific phenomenon of skin aging is known to be associated with cellular damage due to reduction in mucopolysaccharides including hyaluronic acid, collagen crosslinking reaction and ultraviolet rays.

A great deal of research is also being carried out with the aim of inhibiting or improving, e.g., skin wrinkles, fine wrinkles, and sagging, caused by skin damage or skin aging due to ultraviolet exposure. As a result, efficacy has been demonstrated for promoting hyaluronic acid production (JP2001-163794A: Patent document 1), suppressing production and activation of matrix metalloproteinases (MMP) (JP2000-503660X: Patent document 2), promoting production of collagen and inhibiting esterase activation (JP-H11-335235B: Patent document 3), suppression of angiogenesis (WO03/84302A: Patent document 4), and suppressing lymphangiectasis (K. Kajiya et al., Am. J. Pathol., 2006, 169(4): 1496-1503: Non-patent document 1).

Such research is largely divided into efforts to prevent and improve fine wrinkles, with focus on the epidermis or epidermal cells, and efforts to prevent and improve large wrinkles, with focus on suppressing changes in the dermis including blood vessels or lymphatic vessels. Propagation of changes in the epidermis to the dermis leads to alteration of the dermis, including the blood vessels and lymphatic vessels, and heparanase is intricately involved in the process. It has in fact been demonstrated that a significant anti-wrinkle effect is obtained by coating a fine wrinkle model with a heparanase inhibitor (PCT/JP2009/056717).

PRIOR ART DOCUMENTS

Patent Documents

Patent document 1: JP2001-163794A
Patent document 2: JP2000-503660X
Patent document 3: JP-H11-335235B
Patent document 4: WO03/84302A
Patent document 5: DE2746550A
Patent document 6: JP2901297B
Patent document 7: JP2008-303186A
Patent document 8: JP2004-526758X

Non-Patent Documents

Non-patent document 1: K. Kajiya et al., Am. J. Pathol., 2006, 169(4):1496-1503
Non-patent document 2: I. Vlodaysky et al., Semin Cancer Biol., 2002, 12(2):121-129

SUMMARY OF THE INVENTION

Problems to be Solved by the Invention

It is an object of the invention to find a novel drug that is effective for preventing and suppressing skin aging from the viewpoint of the relationship between heparanase and skin aging, and a skin whitener that is effective for preventing and suppressing pigmentation including skin spots, freckles and loss of skin clarity.

Means for Solving the Problems

As a result of much diligent research, the present inventors have found that certain cyclic carboxamide derivatives inhibit heparanase activity, and as a result effectively prevent or suppress aging or pigmentation.

The present application thus provides the invention as set forth below.

(1) A heparanase activity inhibitor comprising, as an active ingredient, a cyclic carboxamide derivative represented by formula (I):

$$\underset{(CH_2)_n}{\overset{X}{\underset{\big|}{\diagup}}}\hspace{-1em}\overset{O}{\underset{N-R^1}{\diagdown\!\!\diagup}} \quad (I)$$

wherein
n is an integer of 1 to 3,
$R^1$ is hydrogen or a C1-6 hydrocarbon group optionally substituted with hydroxyl,
X is —$CH_2$— or a group represented by —N($R^2$)—, where $R^2$ is hydrogen or a C1-6 hydrocarbon group optionally substituted with hydroxyl,
or a salt thereof.

(2) A heparanase activity inhibitor of (1), wherein n=1 in formula (I).

(3) A heparanase activity inhibitor of (1), wherein the cyclic carboxamide derivative is one or more selected from the group consisting of 2-imidazolidinone, 1-(2-hydroxyethyl)-2-imidazolidinone and 1-(2-hydroxyethyl)-2-pyrrolidone.

(4) A wrinkle improving agent comprising a heparanase activity inhibitor of any one of (1) to (3) as an active ingredient.

(5) A large wrinkle improving agent comprising a heparanase activity inhibitor of any one of (1) to (3) as an active ingredient.

(6) A skin whitener comprising a heparanase activity inhibitor of any one of (1) to (3) as an active ingredient.

Effect of the Invention

Since the heparanase activity inhibitor of the invention can efficiently inhibit heparanase activity, it can be used as an active ingredient in a wrinkle improving agent, for example, to prevent or suppress formation of wrinkles (particularly large wrinkles), and may also be suitably used as a skin whitener that is effective for preventing or suppressing pigmentation including skin spots, freckles and loss of skin clarity.

BRIEF DESCRIPTION OF THE DRAWINGS

FIGS. 3(a) and 3(b) are both schematic diagrams of pseudo-skin models, where (a) shows a "heparan sulfate decomposition model," which contains no heparan sulfate on a basal membrane sheet (heparan sulfate (−)), while (b) shows a "normal model," which contains heparan sulfate on a basal membrane sheet (heparan sulfate (+));

FIG. 4 is a graph showing evaluation results for VEGF permeability using the pseudo-skin models of FIGS. 3(a) and 3(b);

FIG. 13 shows results of an in situ bFGF binding assay with seborrheic pigmented tissue.

BEST MODE FOR CARRYING OUT THE INVENTION

Heparanase is present in a variety of cells, as an enzyme that specifically degrades heparan sulfate chains in various types of heparan sulfate proteoglycans. In skin, it is produced by epidermal keratinocytes composing the epidermis and fibroblasts or vascular endothelial cells of the dermis. Its production is also known to be increased in different types of cancer cells, and a connection with cancer malignancy has also been suggested. Increased production of heparanase in cancer cells is known to increase metastasis and increase inducibility of angiogenesis (see I. Vlodaysky et al., Semin Cancer Biol., 2002; 12(2):121-129: Non-patent document 2).

Heparan sulfate proteoglycans have a function of causing extracellular accumulation of heparan sulfate-binding growth factors (e.g., bFGF, HGF, VEGF, and HB-EGF). Perlecan is a type of heparan sulfate proteoglycan that is also present in the epidermal basal membrane at the interface between the epidermis and dermis, and in skin, heparan sulfate-binding growth factors bind to the epidermal basal membrane, controlling migration of growth factors between the epidermis and dermis. In addition, perlecan in the epidermal basal Membrane also controls growth factors for epidermal basal cells that bind to the basal membrane, and it has been shown to be essential for proper growth and differentiation of the epidermis.

Consequently, decomposition of perlecan heparan sulfate chains by activation or accelerated expression of heparanase disturbs the release of accumulated growth factors and control of growth factors in the epidermis and dermis, leading to failure of control of differentiation and growth of the epidermis and thickening of the dermis, and promoting formation of wrinkles. In other words, suppression of heparanase activity suppresses the release of growth factors that accompanies decomposition of heparan sulfate, and helps to suppress migration of growth factors between the epidermis and dermis.

As a result of screening based on heparanase activity as the index, certain cyclic carboxamide derivatives have been found that can significantly suppress heparanase activity. Several compounds are known as cyclic carboxamide derivatives, and for example, they are known for use as skin moisturizers (DE2746550A: Patent document 5), for use as permeation-promoting compounds (JP2901297B: Patent document 6), and for use as cornified envelope formation and maturation promoters (JP2008-303186A: Patent document 7). However, it is completely unknown in the prior art that cyclic carboxamide derivatives exhibit heparanase activity-inhibiting action.

Figure 1:
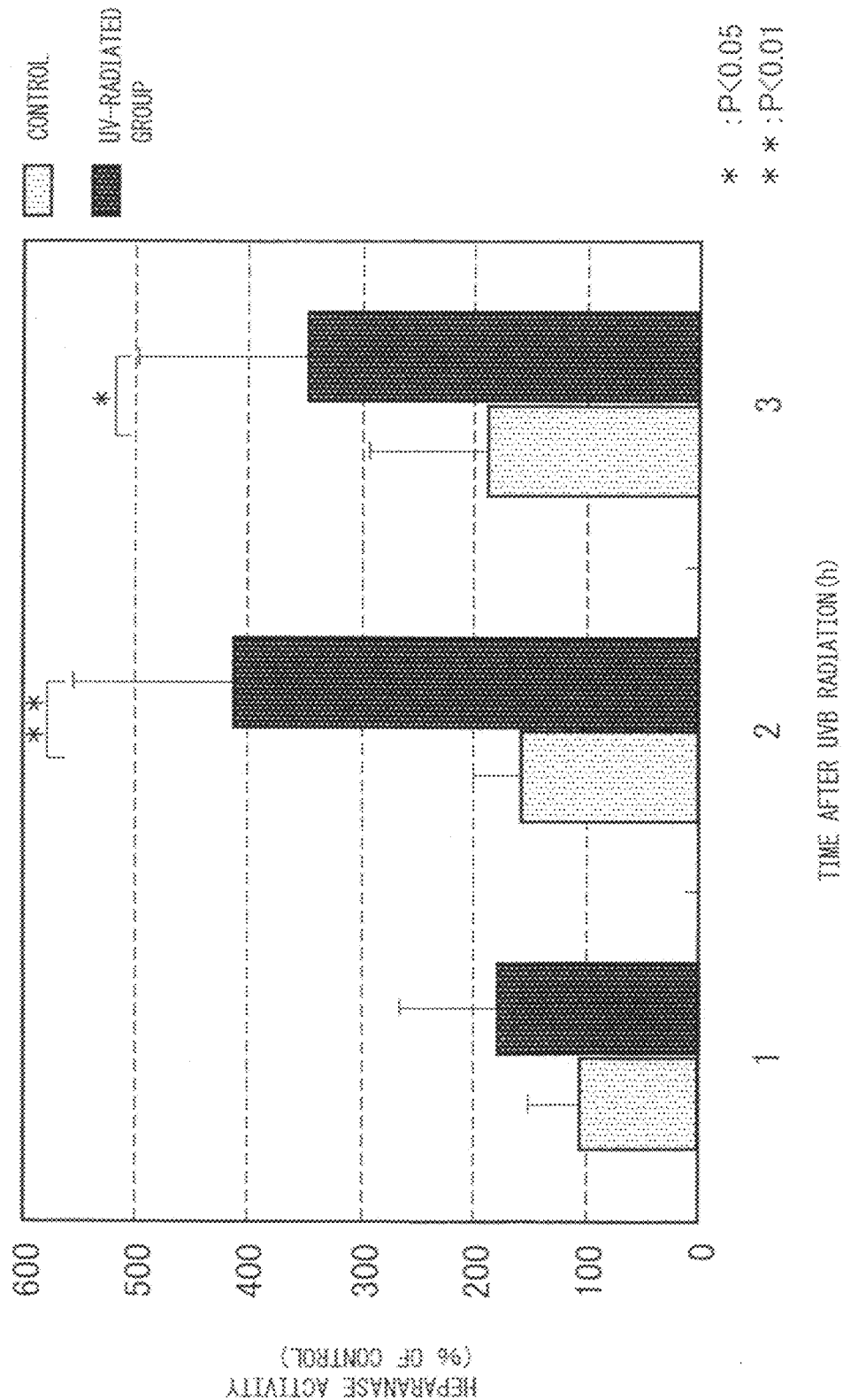
FIG. 1 is a graph showing the difference in heparanase activity in normal human keratinocytes, under ultraviolet-irradiated and non-irradiated conditions.

As explained in detail in the examples, the present inventors have demonstrated that irradiation of cultured normal keratinocytes with ultraviolet rays results in activation of the heparanase of the normal keratinocytes (see FIG. 1). It was also demonstrated that irradiation of human skin with ultraviolet rays increases the amount of heparanase in the epidermis, and reduces heparan sulfate in the basal membrane (see FIG. 2). It was thereby shown that heparanase activation occurs not only in fine wrinkle models but also by ultraviolet rays.

In addition, since basal membrane heparan sulfate is decomposed upon activation of heparanase, the present inventors prepared, as pseudo-skin models, a normal model containing heparan sulfate in a basal membrane and a heparan sulfate-decomposed model containing no heparan sulfate in the basal membrane, and evaluated VEGF permeability and angiogenesis. As a result, it was shown that VEGF permeability was increased and angiogenesis was induced in the heparan sulfate-decomposed model, compared to the normal model (see FIGS. 3 to 6).

Yano et al. have previously indicated that ultraviolet ray-induced induction of angiogenesis in the dermis and alteration of the dermis are important for formation of large wrinkles (JP2004-526758X: Patent document 8), and have found that heparanase is an enzyme intricately involved in not only fine wrinkles but also large wrinkles. That is, inhibition of heparanase activity is effective for not only preventing fine wrinkles due to dryness but also large wrinkles due to prolonged sun exposure. Here, "large wrinkles" is used to mean large, deep wrinkles in the direction perpendicular to the muscle side, that form at the eye corners and in the nasolabial groove, as a result of alterations not only in the epidermis but also the dermis.

In the primary evaluation using heparanase activity as the index, as described in detail in the examples which follow, biotinylated heparan sulfate was immobilized in 96 wells, after which heparanase was allowed to act in the presence of a drug, and the amount of reduction in biotinylated heparan sulfate was used to evaluate the heparanase activity by the reaction with peroxidase-labeled avidin and coloration. Drugs that exhibited a heparanase activity-inhibiting effect in the primary evaluation were then evaluated for reproducibility and concentration-dependence in a secondary evaluation system. In this way it was found that cyclic carboxamide derivatives inhibit heparanase activity.

The term "anti-aging", as used herein, means preventing and improving wrinkles, sagging and hardening of skin by suppressing alteration of skin caused by heparan sulfate-binding growth factors due to decomposition of proteoglycan heparan sulfate in the basal membrane by aging or photoaging, and specifically suppressing epidermal differentiation abnormalities, dermis angiogenesis, lymphangiectasis and elastin breakdown, to maintain an elastic, youthful and healthy state of skin.

Moreover, as described in detail in the examples, the present inventors have also determined that senile pigmented tissue has more decomposition of basal membrane heparan sulfate than light-exposed skin. Decomposition of heparan sulfate leads to loss of control of vascular endothelial growth factor-A (VEGF-A) expressed in the epidermis, whereby alterations occur in the dermal blood vessels and lymphatic vessels causing inflammation, and activation of melanocytes which promotes melanin storage in melanosomes. In addition, failure of control of fibroblast growth factor-7 (FGF-7) expressed in the dermis leads to accelerated delivery of melanosomes from melanocytes to epidermal cells. In other words, the decomposition of heparan sulfate that accompanies heparanase activation is thought to lead to activation of melanocytes due to inflammation and accelerated delivery of melanosomes due to loss of FGF-7 control, resulting in synergistic build-up of melanosomes in keratinocytes. Consequently, a heparanase activity inhibitor is useful not only for preventing and suppressing wrinkles, but also as a skin whitener to prevent and suppress pigmentation including skin spots, loss of skin clarity and freckles.

As used herein, "whitening" means suppressing blackening of skin caused by accumulation of melanosomes in keratinocytes, that occurs with activation of melanocytes accompanying decomposition of heparan sulfate in the basal membrane, thereby improving, e.g., skin spots, freckles, and loss of skin clarity. Unless otherwise specified, the term "whitening method" is used in a cosmetic sense according to the invention, but it may also be used in a medical sense.

The heparanase activity inhibitor of the invention may also be used to treat, improve or prevent other conditions or symptoms associated with heparanase activity. The "conditions or symptoms associated with heparanase activity" may be cancer cell proliferation or metastasis, or angiogenesis. Thus, a medical composition containing a heparanase activity inhibitor of the invention may also be used to suppress cancer cell proliferation or metastasis, or to suppress angiogenesis.

When the cyclic carboxamide derivative of formula (I) according to the invention is a known substance, it may be easily synthesized by a known method or easily purchased as a commercial product, or if it is a novel compound, for example, it may be easily synthesized by a method known to those skilled in the art.

The cyclic carboxamide derivative represented by formula (I) of the invention may also be converted to an inorganic salt or organic salt by a known method. There are no particular restrictions on salts to be used for the invention, and examples include inorganic salts such as hydrochlorides, sulfuric acid salts, phosphoric acid salts, hydrobromic acid salts, sodium salts, potassium salts, magnesium salts, calcium salts and ammonium salts. Organic salts include acetic acid salts, lactic acid salts, maleic acid salts, fumaric acid salts, tartaric acid salts, citric acid salts, methanesulfonic acid salts, p-toluene-sulfonic acid salts, triethanolamine salts, diethanolamine salts and amino acid salts.

The heparanase activity inhibitor of the invention may contain a single type of cyclic carboxamide derivative of formula (I) or its salt alone, but it may also contain two or more cyclic carboxamide derivatives of formula (I) or their salts, in any desired combination and ratio.

The content of the cyclic carboxamide derivative of formula (I) or its salt in the heparanase activity inhibitor of the invention is not particularly restricted so long as it is an amount sufficient to effectively exhibit inhibition against heparanase activity, and it may be appropriately selected according to the purpose of the heparanase activity inhibitor. Generally, however, the proportion of the cyclic carboxamide derivative of formula (I) or its salt with respect to the entire heparanase activity inhibitor is preferred to be usually at least 0.0001 mass % and especially at least 0.0001 mass %, and usually no greater than 1 mass % and especially no greater than 0.2 mass %. When two or more cyclic carboxamide derivatives of formula (I) or their salts are used, the total amount should satisfy the range specified above.

Also, the heparanase activity inhibitor of the invention may further contain any other desired components in addition to the cyclic carboxamide derivative of formula (I) or its salt, so long as the inhibiting effect on heparanase activity by the cyclic carboxamide derivative of formula (I) or its salt is not substantially impaired. Other components include other compounds with inhibiting action on heparanase activity (other active components), or medically acceptable carriers and/or adjuvants. Such other components may be used alone, or two or more may be used in any desired combination and ratio.

The heparanase activity inhibitor of the invention may be produced by a common method, and as a component for an external preparation for skin, one or more of the cyclic carboxamide derivatives of formula (1) or their salts may even be prepared separately, but components commonly used in external preparations for skin, such as quasi drug-containing cosmetics or pharmaceuticals, may be appropriately added as necessary, including oils, surfactants, powders, coloring materials, water, alcohols, thickeners, chelating agents, silicones, antioxidants, ultraviolet absorbers, humectants, aromatics, various drug components, antiseptic agents, pH regulators, neutralizers.

The route of administration and dosage form of the heparanase activity inhibitor of the invention are not restricted, and may be selected as appropriate for the purpose. Examples of routes of administration include local administration (e.g., skin application), oral administration, parenteral administration (e.g., intravenous administration and intraperitoneal administration), and the like, but an external preparation for skin is preferred for use as an anti-aging agent. The dosage form, for local administration (a skin application material), may be a form in which a solution system, solubilized system, emulsified system, powder dispersed system, water/oil two-layer system, water/oil/powder three-layer system or the like, is prepared as a patch, ointment, cream, latex, cosmetic water, gel or aerosol. For oral administration, it may be in the form of a solid preparation such as a tablet, coated tablet, sugar-coated tablet, granules, powder, capsule (e.g., a hard or soft gelatin capsule), or a liquid preparation (solution or suspension) such as an internal liquid drug or syrup. For a parenteral administration, it may be in the form of an injection or the like.

The heparanase activity inhibitor of the invention may also contain one or more other desired components in addition to the cyclic carboxamide derivative of formula (1) or its salt, so long as the inhibiting effect on heparanase activity by the cyclic carboxamide derivative of formula (1) or its salt is not substantially impaired. There are no particular restrictions on such other components, and they may be appropriately selected according to the purpose, dosage form and route of administration of the medical composition, but medically acceptable carriers and/or adjuvants may be mentioned as examples. Examples of adjuvants include diluents, binders, disintegrators, thickeners, dispersing agents, reabsorption accelerators, taste correctives, buffering agents, surfactants, dissolving aids, preservatives, emulsifiers, isotonizing agents, stabilizers and pH regulators.

As specific examples, when the heparanase activity inhibitor of the invention is to be used as an external preparation for skin, components commonly used in external preparations such as skin whiteners, humectants, antioxidants, oil components, ultraviolet absorbers, surfactants, thickeners, alcohols, powder constituents, coloring agents, aqueous components, water or various skin nutrient preparations, may be appropriately added as necessary. In addition, there may also be added appropriate amounts of metal ion chelators such as disodium edetate, trisodium edetate, sodium citrate, sodium polyphosphate, sodium metaphosphate or gluconic acid, antiseptic agents such as methylparaben, ethylparaben or butylparaben, caffeine, tannin, verapamil, tranexamic acid or their derivatives, licorice extract, drug agents such as glabridin, Chinese quince fruit hot water extract, galenicals, tocopherol acetate, glycyrrhizic acid and its derivatives or salts, skin whiteners such as vitamin C, magnesium ascorbate phosphate, glucoside ascorbate, arbutin or kojic acid, saccharides such as glucose, fructose, mannose, sucrose or trehalose, and vitamin A derivatives such as retinoic acid, retinol, retinol acetate or retinol palmitate.

However, these components are not limited to those mentioned above. Such components may also be used in appropriate mixtures, according to formulations for prescribed dosage forms.

The dosage form of the external preparation for skin of the invention is not particularly restricted, and for example, it may be in any desired form such as a solution system, a solubilized system, an emulsified system, a powder-dispersed system, a water-oil two-layer system, a water-oil-powder three-layer system, an ointment, gel, aerosol, or the like. The form of use is also not particularly restricted, and for example, any desired form such as cosmetic water, emulsion, cream, essence, jelly, gel, ointment, pack, mask, foundation or the like may be employed.

The heparanase inhibitor of the invention may be applied to skin for utilization in a cosmetic method to prevent large wrinkle formation, and/or to alleviate and eliminate formed wrinkles. The method and dosage for an external preparation for skin according to the invention used in a beautifying method is not particularly restricted and may be appropriately established depending on the dosage form or the condition of skin wrinkles to be treated, but typically a suitable dose, e.g. from 0.1 ml to 1 ml per $cm^2$ is rubbed directly onto the skin or absorbed in gauze and applied onto the skin, several (1-5) times per day.

The present invention has been explained with concrete examples, with the understanding that these are merely for illustration and that the invention may incorporate any desired modifications that fall within the scope of the claims of the invention.

The present invention will now be explained in greater detail with reference to examples, with the understanding that the invention is not meant to be limited to these examples.

EXAMPLES

1. Evaluation Based on Heparanase Activity Inhibition Rate

A431 cells (human epithelial carcinoma cells) were cultured in 10% serum-containing DMEM (Dulbecco's modified Eagle medium). The cultured cells were solubilized in lysis buffer (50 mM Tris, 0.5% TritonX-100, 0.15 M sodium chloride, pH 4.5) and collected with a scraper, and then pipetted and allowed to stand on ice for 30 minutes. This was followed by centrifugation at 10,000 rpm for 10 minutes to remove the insoluble portion, and the supernatant was recovered as cell extract. The amount of protein in the cell extract was measured with a BCA protein assay kit (BCA Protein Assay Kit, PIERCE, CA46141).

The A431 cell extract was then diluted to 500 μg/mL with assay buffer (50 mM HEPES, 50 mM sodium acetate, 150 mM sodium chloride, 9 mM calcium chloride, 0.1% BSA). Next, the test compound was dissolved in DMSO and added to the diluted cell extract in proportions of 0.0005 mass %, 0.005 mass % and 0.05 mass %, and these were mixed to prepare sample solutions (DMSO final concentration: 5%). A control solution was prepared by mixing DMSO with the diluted cell extract to a final concentration of 5%, and the sample solution and control solution were seeded in a biotinylated heparan sulfate-immobilized plate at 100 μL/well. After reaction at 37° C. for 2 hours and rinsing 3 times with PBS-T, 10,000-fold diluted HRP-avidin (Vector, A-2004)/PBS-T was added at 100 μL/well, and reaction was continued at 37° C. for 1 hour. After further rinsing 3 times with PBS-T, TMB reagent (BIO-RAD, 172-1066) was added at 100 μL/well and reacted therewith, the reaction was terminated with 1N sulfuric acid, and the absorbance at 475 nm (OD475) was measured.

Also, DMSO was added to a serial diluent prepared with the aforementioned A431 cell extract assay buffer (cell extract concentrations: 500 μg/mL, 50 μg/mL, 5 μg/mL, 0.5 μg/mL), to a final concentration of 5% without addition of the test compound, to obtain a mixture (solution for calibration curve). The solution for the calibration curve was subjected to the treatment of the same procedure described above, from seeding of the biotinylated heparan sulfate-immobilized plate, and the OD475 was measured.

Next, a calibration curve for protein concentration was drawn based on the OD475 value of the solution for the calibration curve, and this calibration curve was used to calculate the protein concentration of each sample solution from the OD475 value of a sample solution obtained by adding the test compound at different addition concentrations. The protein concentration was calculated in the same manner for the control solution. The heparanase activity inhibition rate of each sample solution was determined from the ratio of the protein concentration of each sample solution and the protein concentration of the control solution (%).

The details regarding this procedure are described in Japanese Patent Public Inspection No. 2003-502054.

The heparanase activity inhibiting action of different cyclic carboxamide derivatives were tested by this procedure. The results are shown in Table 1. From Table 1 it is seen that each of the cyclic carboxamide derivatives effectively inhibited heparanase activity.

TABLE 1

Heparanase inhibition rate

| Compound | Addition concentration | Inhibition rate |
|---|---|---|
| 1-(2-Hydroxyethyl)-2-imidazolidinone | 0.05% | 99.40% |
| 1-(2-Hydroxyethyl)-2-pyrrolidone | 0.05% | 99.00% |
| 2-Imidazolidinone | 0.5% | 99.95% |
|  | 0.05 | 60.07 |

2. Evaluation of Change in Heparanase Activity by Ultraviolet Radiation.

Normal human keratinocytes were cultured with EpiLife normal keratinocyte medium. The culture medium was temporarily stationed in PBS and then irradiated with 50 mJ UVB, and after culturing for 1 hour, 2 hours and 4 hours, the cells were solubilized with lysis buffer and used as sample solutions in the ultraviolet irradiation group. Also, medium was temporarily stationed in PBS without ultraviolet irradiation, for use as a control solution. The sample solutions and control solution were used for treatment in the same manner as Example 1, and the OD475 was measured. The heparanase activities were evaluated in the same manner as Example 1, based on the obtained OD475 values. The results are shown in FIG. 1. It was shown that heparanase was significantly activated in the ultraviolet irradiation group compared to the non-irradiated control.

Figure 2:
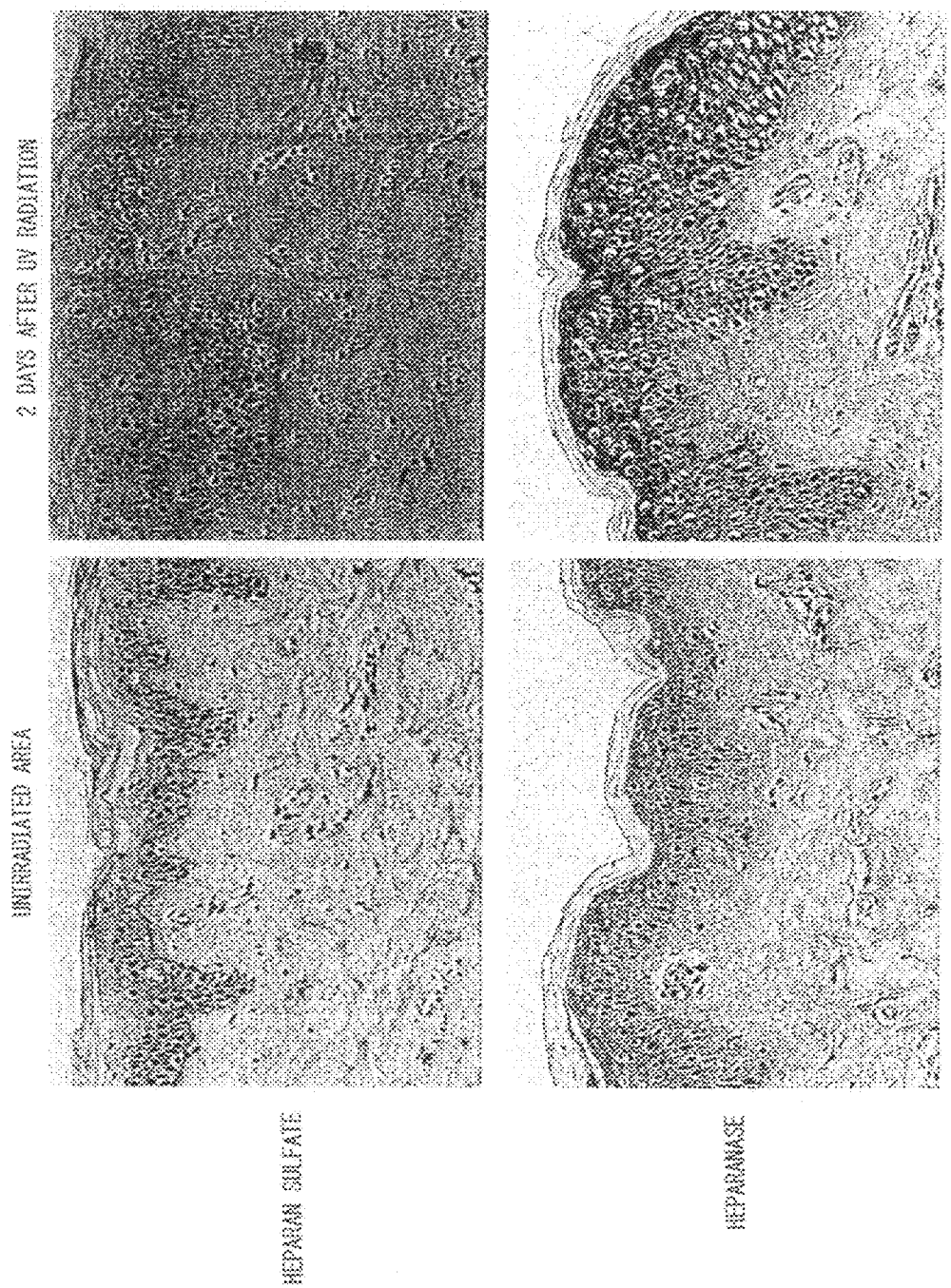
FIG. 2 is a set of immunostaining images for heparanase and heparan sulfate in ultraviolet-irradiated and non-irradiated sections of normal human buttock tissues.

Immunostaining of Heparanase and Heparan Sulfate in Ultraviolet-Irradiated Human Skin Human gluteus (20-year-old) was irradiated with 2MED ultraviolet rays, and after 2 days the irradiated section and surrounding non-irradiated buttock skin were biopsied, and a paraffin block was formed by the AMeX method. A 3 µm tissue section was formed, and the heparanase and heparan sulfate were immunostained. The obtained immunostaining image is shown in FIG. 2. The amount of heparanase was clearly increased and the heparan sulfate content reduced in the ultraviolet irradiated section, compared to the non-irradiated section.

Evaluation of VEGF Permeability and Angiogenesis with and without Heparan Sulfate After heating and dissolving 2 mg of heparan sulfate and 10 mg of agarose in 1 ml of PBS (1% agarose solution), it was coated with an insert (24-well Transwell by Corning, Inc.) to form a heparan sulfate-containing sheet. As a control, a sheet containing no heparan sulfate was formed by the same procedure, except that agarose alone was used, without using heparan sulfate. Thus, the insert interior was selected for the epidermis side, the sheet as the basal membrane, and the well on the dermis side, to prepare a pseudo-skin model (FIG. 3a, b).

The obtained pseudo-skin model can be used as an evaluation system for evaluating VEGF permeability and angiogenesis, based on the presence or absence of heparan sulfate in the sheet selected as the basal membrane (hereinafter referred to as "basal membrane sheet"). In the explanation which follows, the pseudo-skin model containing heparan sulfate in the basal membrane sheet is referred to as the "normal model", and the pseudo-skin model containing no heparan sulfate in the basal membrane sheet is referred to as the "heparan sulfate-decomposed model".

First, for evaluation of the VEGF permeability, a 10 µg/mL VEGF aqueous solution was added to the epidermis side (insert interior) of each model and allowed to stand for 3 hours at room temperature, and the VEGF concentration in the well on the dermis was detected with a VEGF ELISA kit (R&D systems). The results are shown in FIG. 4. The VEGF permeation was significantly reduced in the normal model compared to the heparan sulfate-decomposed model.

Figure 5:
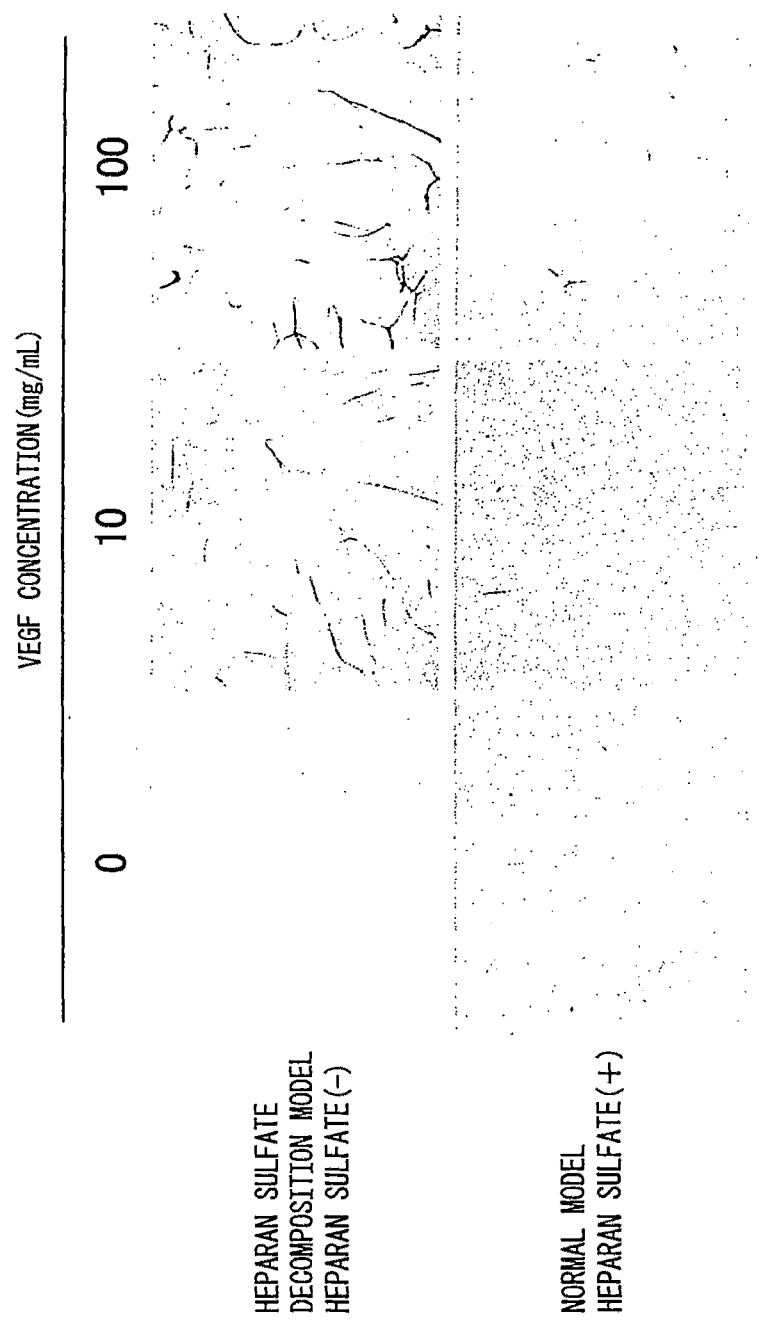
FIG. 5 is a set of photographs showing evaluation results for angiogenesis using the pseudo-skin models of FIGS. 3(a) and 3(b)

Next, for evaluation of angiogenesis, a 100 µg/mL VEGF aqueous solution was added to the epidermis side (insert interior) of each model, and set in an angiogenesis kit (Kurabo Industries, Ltd.) for culturing for 11 days, after which an optical microscope photograph of the culture was taken. The obtained image is shown in FIG. 5. Notable angiogenesis was observed in the heparan sulfate-decomposed model in a concentration dependent manner, while no angiogenesis was observed in the normal model.

Figure 6:
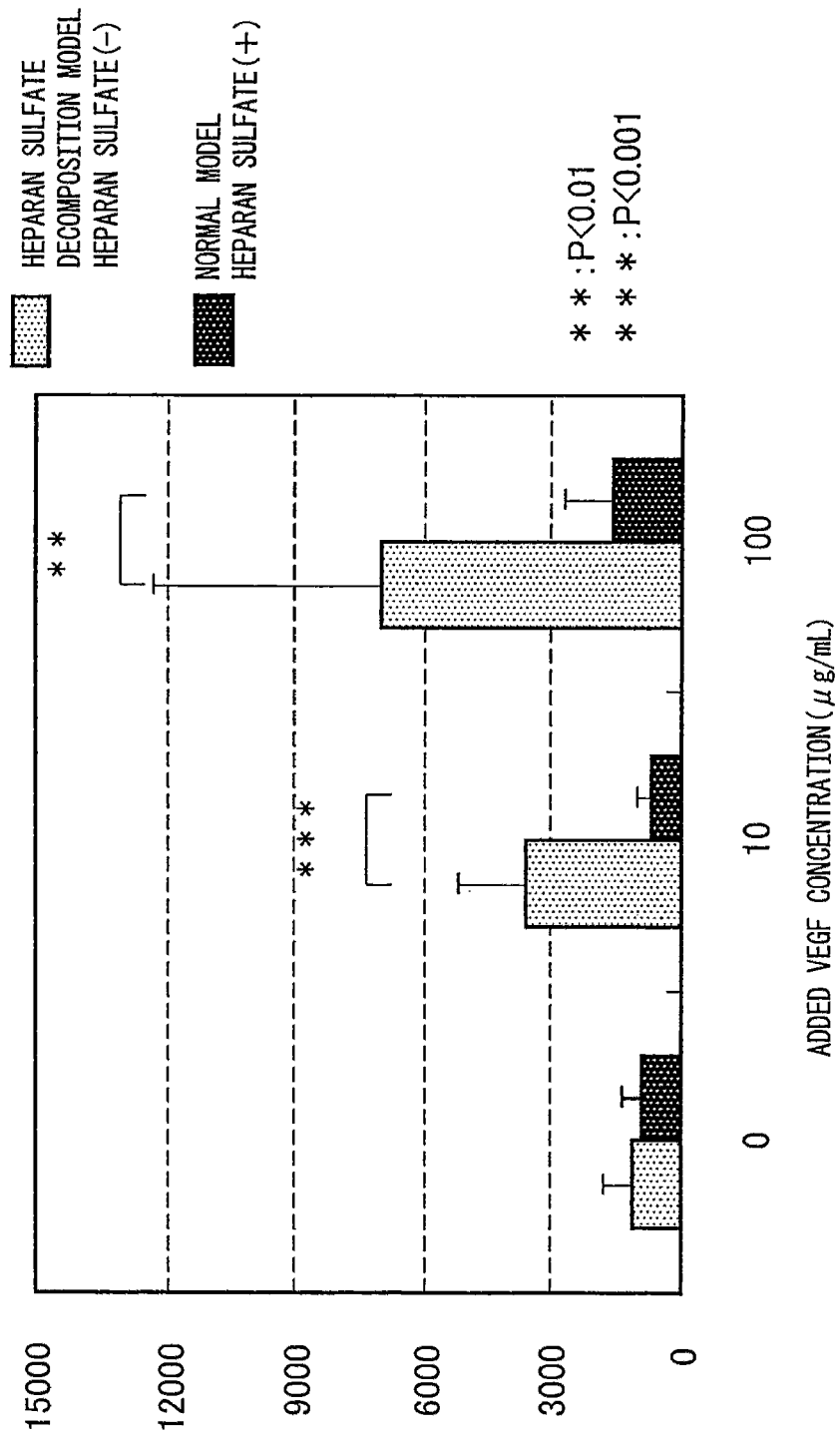
FIG. 6 is a graph showing the analysis results for blood vessel area in the photograph of FIG. 5.

Angiogenesis kit analysis software (Kurabo Industries, Ltd.) was used to analyze the blood vessel area in the image of FIG. 5. The results are shown in FIG. 6. A notable increase in blood vessel area was observed in the heparan sulfate-decomposed model compared to the normal model, demonstrating significant angiogenesis.

3. Evaluation of Whitening Effect with Heparanase Inhibitor

A melanocyte-containing skin model was used to examine the whitening effect of the heparanase inhibitor 1-[4-(1H-benzimidazol-2-yl)-phenyl]-3-[4-(1H-benzimidazol-2-yl)-phenyl]-urea.

Culturing of a melanocyte-containing skin model (MEL-FT, manufactured by MatTeK, USA) was initiated in special medium (MEL-FT-NMM-113, manufactured by MatTeK, USA). From the second day of culturing, DMSO was added in the control group and 1-[4-(1H-benzimidazol-2-yl)-phenyl]-3-[4-(1H-benzimidazol-2-yl)-phenyl]-urea was added to a final concentration of 50 µM in the heparanase inhibitor group, and culturing was continued with medium exchange every 2 or 3 days. On the 10th and 14th days of culturing, the skin model was sampled and an appearance photograph was taken, whereby the color in the heparanase inhibitor group was found to be faintly white compared to the control group.

The epidermis alone of the skin model was then sampled, a 300 µL 0.2N sodium hydroxide solution was added, and the mixture was stirred and allowed to stand for 24 hours at room temperature, and then heated for 30 minutes at 95° C. for complete solubilization of the epidermis. When the melanin content in the epidermis was examined by measuring the absorbance of the solubilized solution at 475 nm, the heparanase inhibitor group clearly had a significantly lower OD475 nm value, i.e. a lower melanin content, compared to the control group.

Figure 7:
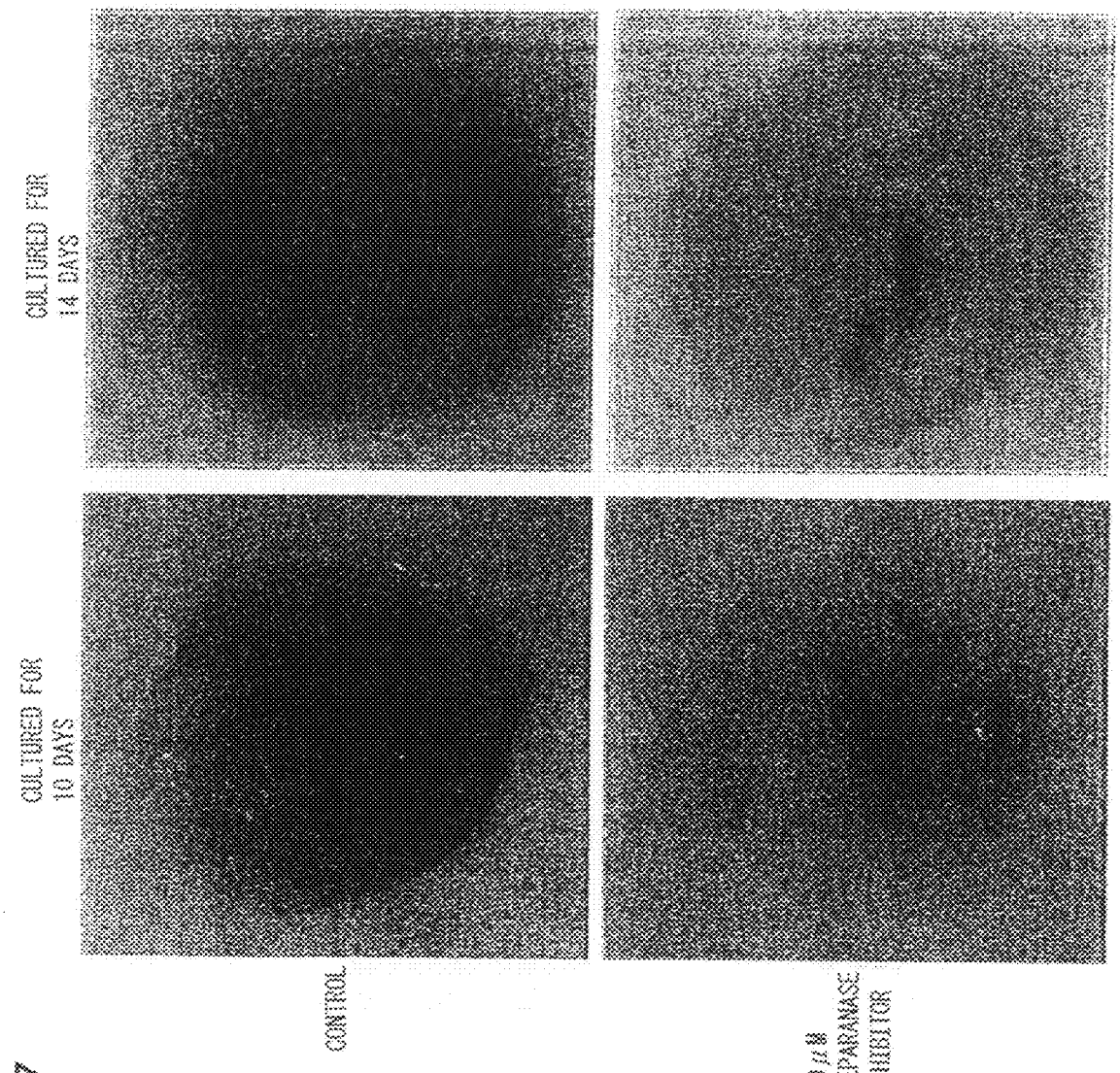
FIG. 7 is a set of photographs for the appearance of a melanocyte-containing skin model (MEL-FT, manufactured by MatTeK, USA)
Figure 8:
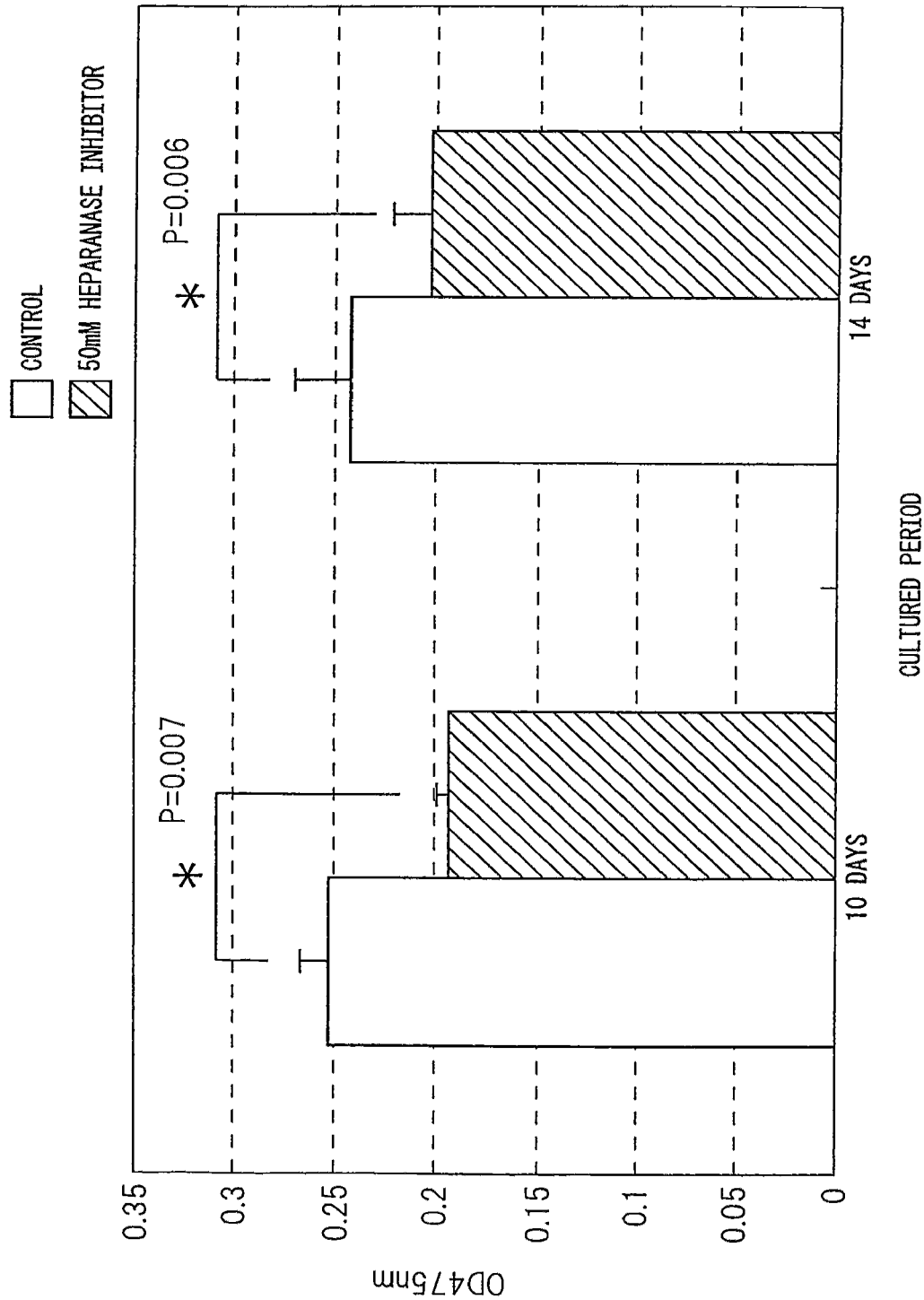
FIG. 8 is a graph showing comparative results for melanin content in epidermis for different skin models.

FIG. 7 shows an appearance photograph of the MEL-FT skin model. Whiteness was clearly seen in the heparanase inhibitor group by the 10th and 14th days of culturing. FIG. 8 shows comparative results for melanin content in the epidermis for each skin model. On the 10th and 14th days of culturing, the absorbance value at OD475 nm as an indicator of melanin was dominantly low in the heparanase inhibitor group. The heparanase inhibitor was thus demonstrated to have a whitening effect.

4. Immunostaining of Lyophilized Human Tissue

A lyophilized tissue block of a senile pigmentation spot and the surrounding normal skin were freshly microtomed to prepare 8 µm strips. The tissue strips sliced to 8 µm were fixed with cold acetone and dried, and the OCT was removed with PBS. After deactivation of the endogenous peroxidase by 3% hydrogen peroxide water treatment, it was subjected to blocking with 10% normal goat serum, and reaction was conducted with the primary antibody and secondary antibody listed in Table 1, in that order. The HRP-labeled tissue was rinsed 5 times with PBS, and then colored with AEC. The colored tissue was thoroughly rinsed with running water and then encapsulated using a water-soluble mounting agent.

TABLE 2

Primary and secondary antibodies used

| Primary antibody | Immune animal | Manufacturer | Secondary antibody | Manufacturer |
|---|---|---|---|---|
| CD31 | Mouse | DAKO | EnVision-mouse Ig | Nichirei |
| LYVE1 | Rabbit | Upstate | EnVision-rabbit Ig | Nichirei |
| Perlecan | Rat | Chemicon | Biotinylated rat Ig | DAKO |
| Heparan sulfate | Mouse | Seikagaku | Biotinylated mouse IgM | Vector |

5. In situ bFGF Assay

After binding 25 μg of bFGF to 200 μL of swelled heparin-Sepharose (CL-6B; Pharmacia Biotech), this was reacted with $NH_2$-reactive biotin (Dojindo molecular tech.) dissolved in DMSO for 5 minutes at room temperature, rinsed with 800 μL of rinsing buffer (20 mmol/L HEPES, pH 7.4, 400 mmol/L NaCl), and eluted twice with 200 μL of elution buffer (20 mmol/L HEPES, pH 7.4, 0.2% BSA, 3 mol/L NaCl), to recover high-salt-concentration biotinylated bFGF. It was then placed in an Ultra free C3LGC column (Amicon) and rinsed 3 times with PBS to obtain (0.25 g/L) biotinylated bFGF.

Paraffin tissue strips (senile, seborrheic keratosis and surrounding normal sections) cut to 5 μm were deparaffinated with xylene and then exchanged with ethanol (100%→70%) and the endogenous peroxidase was inactivated by 3% hydrogen peroxide water treatment. They were then rinsed with pH 5 buffer (containing 0.5 M NaCl) and pH 10 buffer (containing 0.5 M NaCl), to release the endogenous heparan sulfate bonding factors. Blocking was performed with 10% serum, followed by reaction with biotinylated bFGF (10 nmol/L) at room temperature for 1 hour and rinsing 3 times with PBS. This was further followed by reaction with peroxidase-labeled streptavidin (Nichirei, Japan) at room temperature for 15 minutes, rinsing 3 times with PBS, and coloring with DAB. The colored tissue was thoroughly rinsed with running water, and after staining the nuclei with haematoxylin and performing ethanol exchange (70%→4100%) and xylene substitution, it was encapsulated.

6. Image Analysis of Blood Vessels and Lymphatic Vessels

CD31-stained and LYVE1-stained tissue was photographed 3 times per slice, and the number of stained blood vessels and lymphatic vessels and the area were calculated by image analysis, using WinROOF (Mitani Corporation). In addition, the total area of dermis in the dermis papillary layer area was also calculated by image analysis, and the density and sizes of the blood vessels or lymphatic vessels were calculated.

Figure 9:
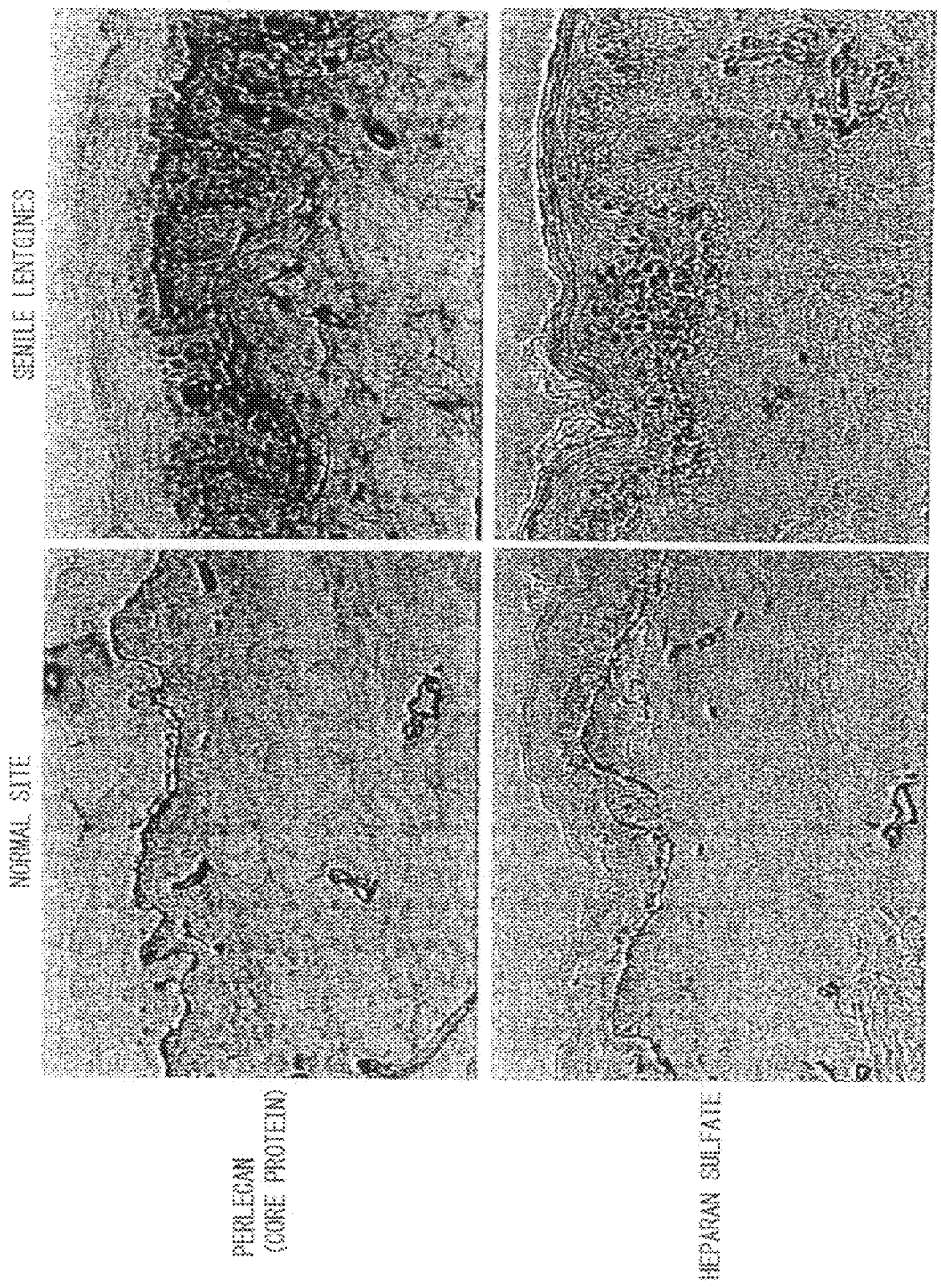
FIG. 9 shows immunostaining results for perlecan and heparan sulfate in senile pigmentation spots and in surrounding normal tissue.

FIG. 9 shows immunostaining results for perlecan and heparan sulfate in senile pigmentation spots and in surrounding normal tissue. The basal membrane was stained with both perlecan and heparan sulfate in the normal tissue, but stained only by perlecan staining in the senile pigmented tissue, while heparan sulfate staining was notably reduced. These results indicate that heparan sulfate had been specifically degraded in the senile pigmentation spot sections.

Figure 10:
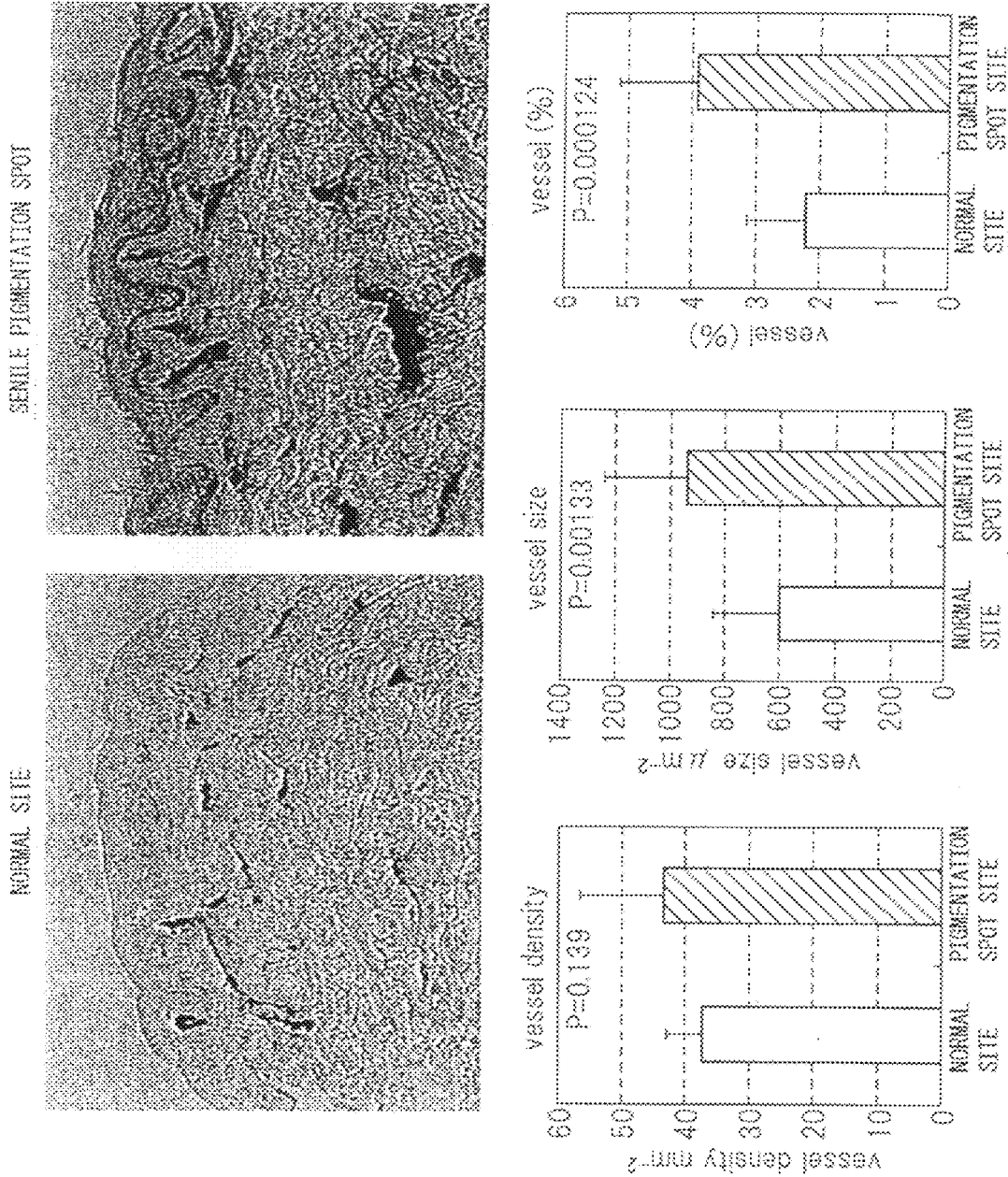
FIG. 10 shows results of immunostaining with anti-CD31 antibody as a vascular marker, together with image analysis results.

FIG. 10 shows results of immunostaining with anti-CD 31 antibody as a vascular marker, together with image analysis results. The number, thickness and area of the CD31-stained blood vessels was calculated with the image analysis software WinROOF for each stained image, and the change in blood vessels in the senile pigmentation spot sections and surrounding normal sections was analyzed. The blood vessel sizes and blood vessel areas were found to be significantly higher in the senile pigmentation spot sections. These results indicated that vasodilation had occurred in the senile pigmentation spot sections.

Figure 11:
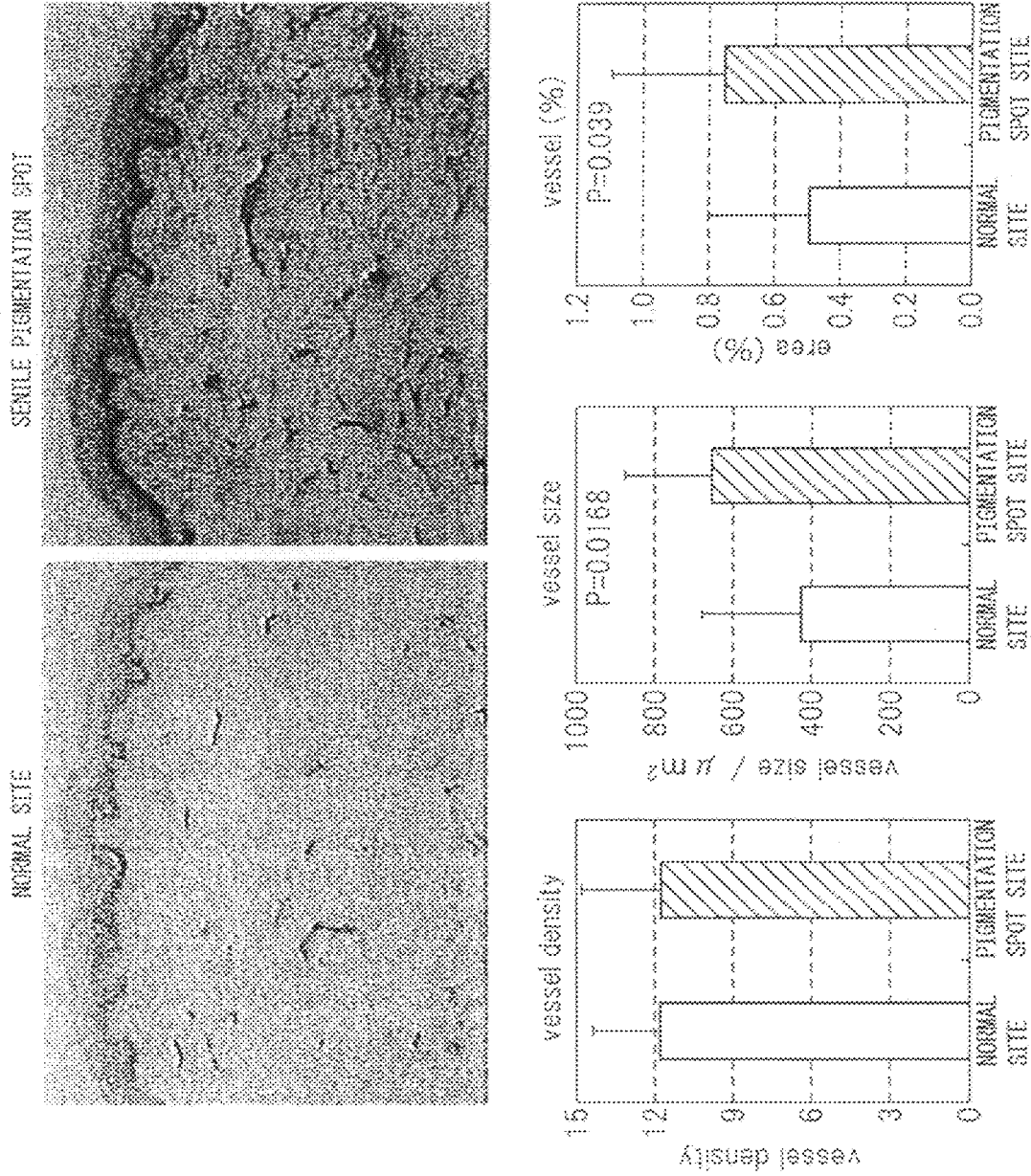
FIG. 11 shows results of immunostaining with anti-LYVE-1 antibody as a lymphatic marker, together with image analysis results.

FIG. 11 shows results of immunostaining with anti-LYVE-1 antibody as a lymphatic marker, together with image analysis results. The number, thickness and area of the LYVE-1-stained lymphatic vessels was calculated with the image analysis software WinROOF for each stained image, and the change in lymphatic vessels in the senile pigmentation spot sections and surrounding normal sections was analyzed. The lymphatic vessel sizes and lymphatic vessel areas were found to be significantly higher in the senile pigmentation spot sections. These results indicated that lymphangiectasis had occurred in the senile pigmentation spot sections.

Figure 12:
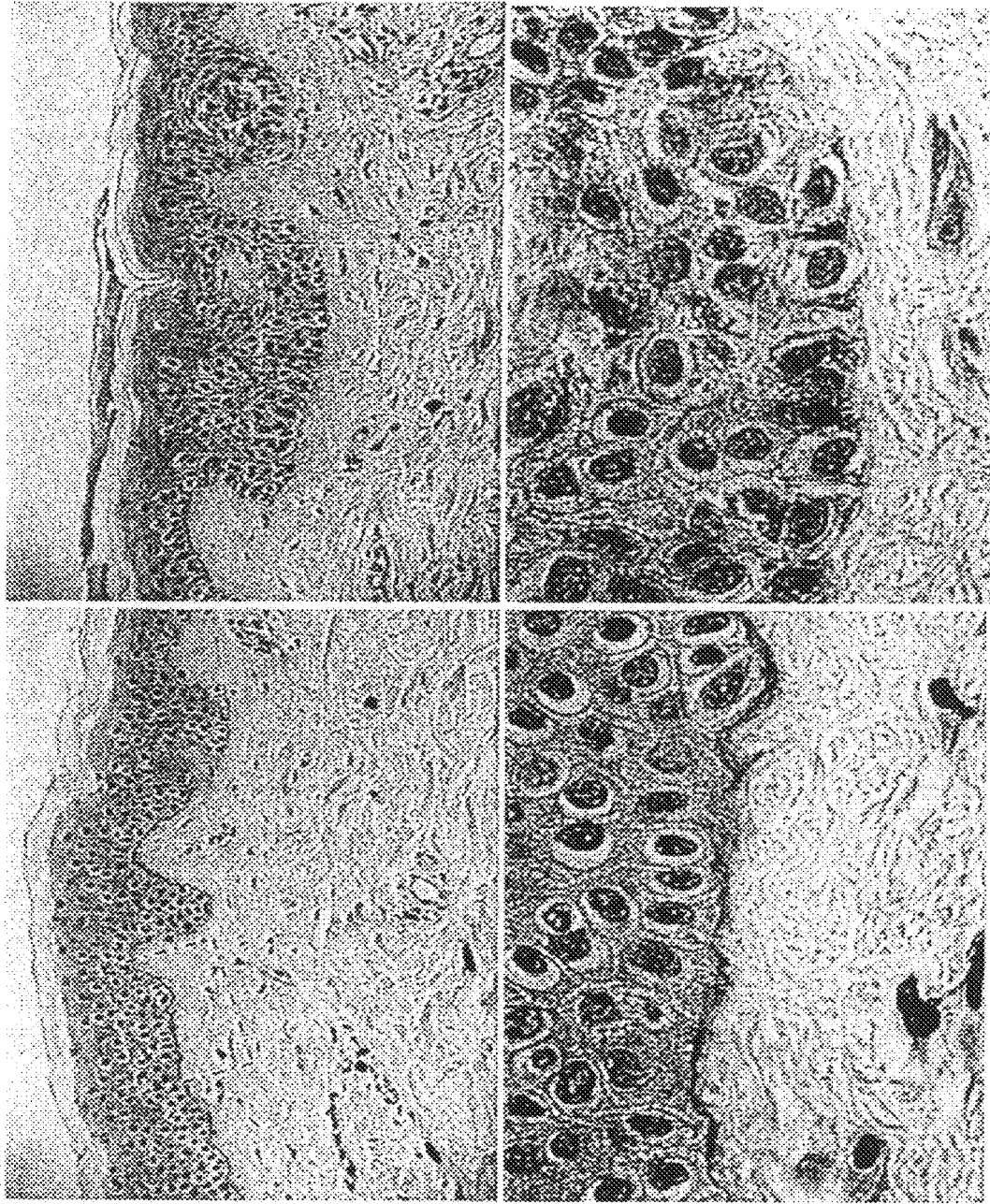
FIG. 12 shows results of an in situ bFGF binding assay with senile pigmented tissue.

FIG. 12 shows the results of an in situ bFGF binding assay with senile pigmented tissue. Here it is shown that the basal membrane was colored brown in the normal tissue surrounding the senile pigmentation spots, indicating bFGF binding, whereas no staining of the basal membrane is seen, i.e. bFGF was not capable of binding, in the senile pigmentation spot sections, suggesting that bFGF binding was no longer possible due to degradation of heparan sulfate.

FIG. 13 shows the results of an in situ bFGF binding assay with seborrheic pigmented tissue. Here it is shown that the basal membrane was colored brown in the normal tissue surrounding the seborrheic pigmentation spots, indicating bFGF binding, whereas no staining of the basal membrane is seen, i.e. bFGF was not capable of binding, in the seborrheic pigmentation spot sections, suggesting that bFGF binding was no longer possible due to degradation of heparan sulfate.

Industrial Applicability

Since the heparanase activity inhibitor of the invention can efficiently inhibit heparanase activity, it can be used as an active ingredient in a wrinkle improving agent, for example, to prevent or suppress formation of wrinkles (particularly large wrinkles), or to prevent or suppress pigmentation including skin spots, freckles and loss of skin clarity.

The invention claimed is:

1. A method for whitening skin, comprising the step of administering, to a subject in need thereof, 1-(2-hydroxyethyl)-2-imidazolidinone.

* * * * *